(12) United States Patent
Johnson et al.

(10) Patent No.: US 7,801,612 B2
(45) Date of Patent: Sep. 21, 2010

(54) SYSTEM AND METHOD FOR MANAGING LOCALLY-INITIATED MEDICAL DEVICE INTERROGATION

(75) Inventors: David C. Johnson, Inver Grove Heights, MN (US); Howard D. Simms, Shoreview, MN (US); Kenneth P. Hoyme, Plymouth, MN (US); Muralidharan Srivathsa, Shoreview, MN (US); Benjamin L. Somberg, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1089 days.

(21) Appl. No.: 11/447,523

(22) Filed: Jun. 5, 2006

(65) Prior Publication Data

US 2007/0282634 A1     Dec. 6, 2007

(51) Int. Cl.
*A61N 1/08* (2006.01)
(52) U.S. Cl. .............................. 607/32; 607/27; 600/301
(58) Field of Classification Search ................. 128/903; 607/27, 32, 59, 60; 600/301; 705/2, 3
See application file for complete search history.

(56) References Cited

U.S. PATENT DOCUMENTS

| 6,024,699 | A  | 2/2000  | Surwit et al. |
|-----------|----|---------|---------------|
| 6,083,248 | A  | 7/2000  | Thompson |
| 6,168,563 | B1 | 1/2001  | Brown |
| 6,171,256 | B1 | 1/2001  | Joo et al. |
| 6,263,245 | B1 | 7/2001  | Snell |
| 6,336,903 | B1 | 1/2002  | Bardy |
| 6,368,284 | B1 | 4/2002  | Bardy |
| 6,398,728 | B1 | 6/2002  | Bardy |
| 6,411,840 | B1 | 6/2002  | Bardy |
| 6,416,471 | B1 | 7/2002  | Kumar et al. |
| 6,418,346 | B1 | 7/2002  | Nelson et al. |
| 6,440,066 | B1 | 8/2002  | Bardy |
| 6,827,670 | B1 | 12/2004 | Stark et al. |
| 2003/0114898 | A1* | 6/2003 | Von Arx et al. ............... 607/60 |
| 2004/0103001 | A1 | 5/2004 | Mazar et al. |
| 2004/0259494 | A1 | 12/2004 | Mazar |
| 2005/0195930 | A1* | 9/2005 | Spital et al. ................. 375/368 |
| 2006/0253300 | A1 | 11/2006 | Somberg et al. |
| 2006/0253301 | A1 | 11/2006 | Simms et al. |
| 2010/0063840 | A1 | 3/2010 | Hoyme et al. |

OTHER PUBLICATIONS

Health Insurance Portability and Accountability Act of 1996, Pub. L. No. 104-191, 110 Stat. 1936 (Aug. 21, 1996).

(Continued)

*Primary Examiner*—Carl H Layno
*Assistant Examiner*—Pamela M Bays
(74) *Attorney, Agent, or Firm*—Pauly, DeVries, Smith & Deffner, L.L.C.

(57) ABSTRACT

A system and method for managing locally-initiated medical device interrogation is presented. A noncontinuously coupleable interface is provided over which to retrieve patient data recorded and transiently staged by a medical device monitoring physiological measures of a patient. The patient data is periodically retrieved by interfacing to and interrogating the medical device per a pre-defined schedule defining autonomous patient data retrieval frequency. Further retrieval of the patient data is permitted independent of the pre-defined schedule by enabling operation of the interface based on a remotely-specifiable criteria for controlling locally-initiated patient data retrieval.

24 Claims, 9 Drawing Sheets

OTHER PUBLICATIONS

E. Hammond, "National Committee on Vital and Health Statistics, Subcommittee on Health Data Needs, Standards And Security," http://www.ncvhs.hhs.gov/970211t3.htm, pp. 1-4 (Feb. 11, 1997).
Security And Electronics Signature Standards; Proposed Rule, Federal Register, vol. 63, No. 155 (Aug. 12, 1998).
"St. Jude Medical Launches the Housecall Plus Remote Monitoring System", St. Jude Medical, Inc., http://www.medscape.com/pages/editorial/pressreleases/pr-crm-sjm30 (May 14, 2004) (2 pgs.).
Medtronic Carelink Programmer, "Model 2090 Programmer/Model 2290 Analyzer for Medtronic and Vitatron Devices", Analyzer Reference Guide (Apr. 12, 2005) (89 pgs.).
Medtronic Carelink Programmer, "Model 2090 Programmer/Model 2290 Analyzer for Medtronic and Vitatron Devices", Programmer Reference Guide (Nov. 7, 2005) (105 pgs.).

* cited by examiner

SYSTEM AND METHOD FOR MANAGING LOCALLY-INITIATED MEDICAL DEVICE INTERROGATION

FIELD OF THE INVENTION

The invention relates in general to automated patient management and, specifically, to a system and method for managing locally-initiated medical device interrogation.

BACKGROUND OF THE INVENTION

Chronic disease patients require clinical follow-up at intervals that can vary widely, depending upon the type and stage of disease involved. For instance, implantable medical device (IMD) recipients receive follow-up every three to twelve months during which their IMD is interrogated to retrieve patient data recorded since the follow-up. Generally, IMDs are interrogated either through induction, using a wand physically connected to a programmer or through radio frequency (RF) telemetry, which only requires close physical proximity. As necessary, the IMD can be reprogrammed to modify the treatment profile.

Patient management devices are at-home, patient-operable devices that perform functions similar to programmers, yet allow IMD recipients and external medical device (EMD) users to be remotely managed by caregivers without the time, expense, and inconvenience of office visits. Patient management devices allow ambulatory follow-up outside of a clinical setting that can also be performed more frequently than would otherwise be possible in-clinic. Caregivers, through patient management devices, can remotely interrogate and retrieve patient data for centralized evaluation, as well as to ensure patient compliance with prescribed treatment regiments. In addition, patients can perform self-initiated interrogations, presumptively in response to caregiver instructions or following an event occurrence.

Patient-initiated medical device interrogation serves as a helpful adjunct to regular patient following by capturing physiometry closer in time to events of potential medical concern. However, patient-initiated interrogation also presents a potential for abuse due to, for instance, patients psychologically nervous or overly-concerned with the operation of their medical devices. Education can allay some patient concerns, but an unrestricted ability to self-interrogate can still create serious non-health-related problems if unchecked. Each medical device interrogation, whether scheduled or patient-initiated, creates a set of retrieved patient data, which is subsequently uploaded to a centralized repository for caregiver review and evaluation. Over-interrogation, particularly of implantable medical devices, can lead to premature battery depletion, potentially necessitating early implant replacement. Moreover, additional caregiver resources may be required to track unsolicited patient data and reimbursement may not be available for following unsolicited patient data. Furthermore, caregivers are potentially exposed to liability if uninformed of the receipt of new unsolicited patient data. Conventional medical device interrogation approaches control scheduled and patient-initiated interrogation identically.

U.S. Pat. No. 6,168,563, to Brown, discloses enabling a healthcare provider to monitor and manage a patient's health condition. A clearinghouse computer communicates with the patient through a data management unit, which interactively monitors the patient's health. Patient information may be supplied by physiological monitoring devices, such as blood glucose monitors or peak-flow meters. Healthcare providers access the patient information through the clearinghouse computer, which can process, analyze, print, and display the data. Although the data management unit can interface to external medical devices, Brown fails to disclose remotely controlling and coordinating on-going patient care through managed medical device interrogation.

U.S. Pat. No. 6,418,346 issued Jul. 9, 2002, to Nelson et al., describes remote patient therapy and diagnosis that includes a personal data manager (PDM) used in a Web-based network. The PDM cooperates with a programmer to remotely monitor IMDs. The PDM is implemented to forward information to personal computers or to uplink data from a programmer to a Web-based export data center. The PDM provides an extension to the programmer and operates as a data retrieval messenger between the programmer, export data center, and IMDs. However, Nelson fails to disclose controlling medical device interrogation.

U.S. Pat. No. 6,263,245 issued Jul. 17, 2001, to Snell, describes portable implantable device interrogation through wireless interrogation of an IMD. A portable interrogation device can be directly interfaced with a data processing device, such as a programmer/analyzer. The portable interrogation device includes a control circuit for controlling telemetry transmission, a transmitter for sending signals, a receiver for receiving data from an IMD in response to interrogation signals, a memory for storing data received, and an electronic communications interface for high-speed delivery of data to the data processing device. However, Snell fails to disclose remotely controlling medical device interrogation frequency and enablement.

Therefore, there is a need for providing remote control over patient-initiated medical device interrogations without interrupting regular follow-up of patient data retrieval or altering the on-board programming of medical devices, particularly IMDs.

SUMMARY OF THE INVENTION

A system and method includes a patient management device that interfaces to one or more medical devices, including implantable and external medical devices and monitors. A caregiver-specified schedule defines the frequency of autonomous patient data retrieval from the medical devices. Caregiver-specified criteria define the permissibility, conditionality, and maximum permissible occurrences of patient-initiated medical device interrogation. The schedule and criteria define mutually exclusive controls over the operation of the patient management device under which the scheduled autonomous medical device interrogations proceed independently of patient-initiated interrogation.

One embodiment provides a system and method for managing locally-initiated medical device interrogation. A non-continuously coupleable interface is provided over which to retrieve patient data recorded and transiently staged by a medical device monitoring physiological measures of a patient. The patient data is periodically retrieved by interfacing to and interrogating the medical device per a pre-defined schedule defining autonomous patient data retrieval frequency. Further retrieval of the patient data is permitted independent of the pre-defined schedule by enabling operation of the interface based on a remotely-specifiable criteria for controlling locally-initiated patient data retrieval.

Still other embodiments will become readily apparent to those skilled in the art from the following detailed description, wherein are described embodiments of the invention by way of illustrating the best mode contemplated for carrying out the invention. As will be realized, the invention is capable of other and different embodiments and its several details are capable of modifications in various obvious respects, all without departing from the spirit and the scope of the present invention. Accordingly, the drawings and detailed description are to be regarded as illustrative in nature and not as restrictive.

DETAILED DESCRIPTION

Implantable Medical Device

Figure 1:
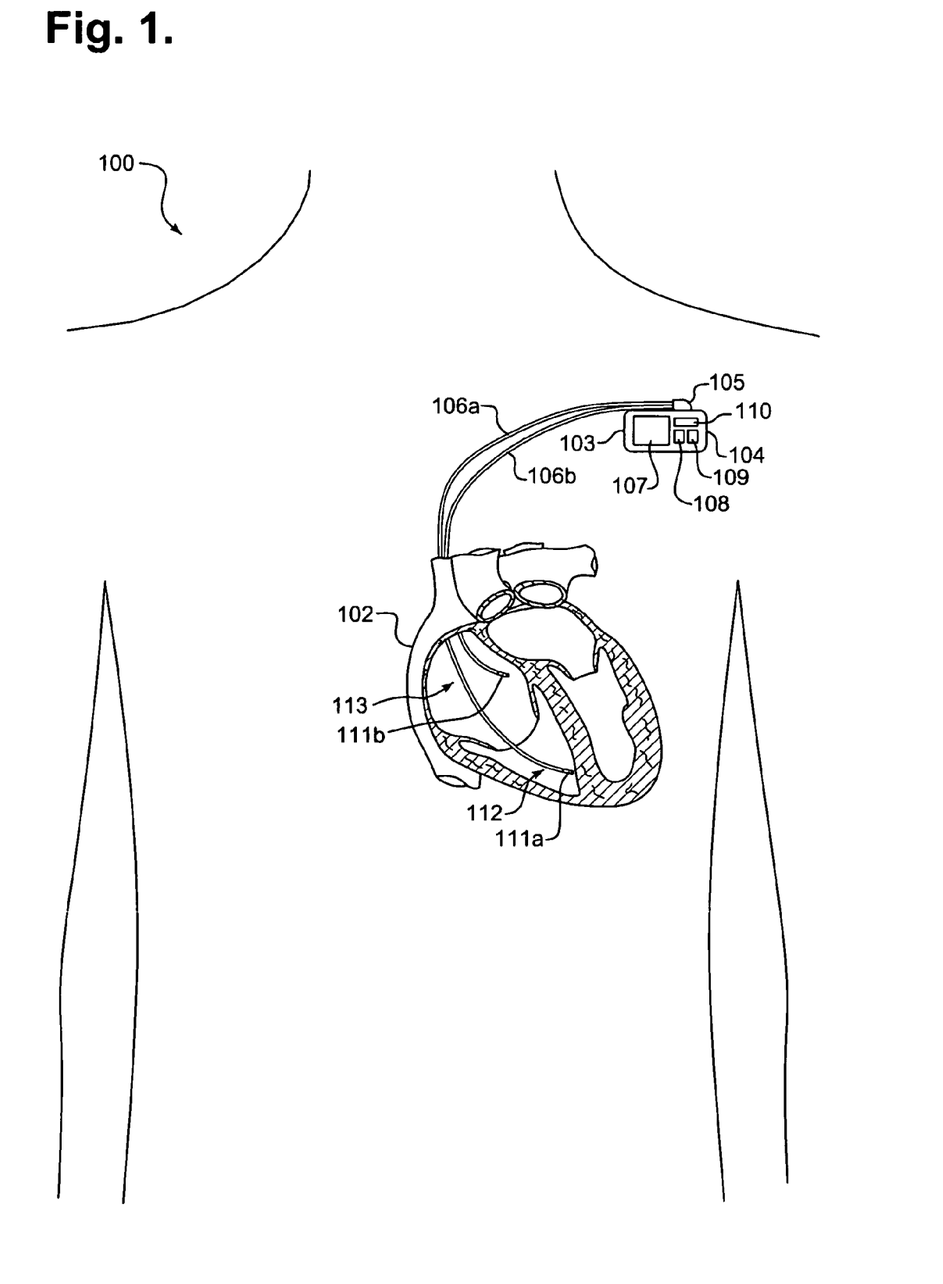
FIG. 1 is a block diagram showing, by way of example, an implantable medical device for use with one embodiment.

Remote patient care can be provided for recipients of implantable medical devices (IMDs) or external medical devices (EMDs), although the interfaces for accessing IMDs are more specialized and limited than the interfaces used with EMDs. FIG. 1 is a block diagram 100 showing, by way of example, an IMD 103 for use with one embodiment. The IMD 103, such as a cardiac pacemaker, implantable cardiac defibrillator (ICD), cardiac resynchronization device, or similar medical device, is surgically implanted in the chest or abdomen of a patient to provide in situ therapy, such as pacing, defibrillation, cardiac resynchronization, neural stimulation, drug delivery, and physiological data monitoring and collection. Examples of IMDs suitable for use in the described embodiment include the Pulsar Max II, Discovery, and Discovery II pacing systems and the Contak Renewal cardiac resynchronization therapy defibrillators, sold by Guidant Corporation, St. Paul, Minn.

The IMD 103 includes a case 104 and terminal block 105 electrically coupled to a set of therapy leads 106a-b. The leads 106a-b are implanted transvenously for endocardial placement. The IMD 103 is in direct electrical communication with the heart 102 through electrodes 111a-b positioned on the distal tips of each lead 106a-b. By way of example, the set of leads 106a-b can also include a right ventricular electrode 111a and right atrial electrode 111b to enable the IMD 103 to directly collect physiological measures, preferably through millivolt measurements.

The IMD case 104 houses hermetically-sealed components, including a battery 107, control circuitry 108, memory 109, and telemetry circuitry 110. The battery 107 provides a finite power source. The control circuitry 108 controls therapy delivery and patient physiometry monitoring, including the delivery of electrical impulses, or "shocks," to the heart 102 and sensing of spontaneous cardiac electrical activity. The memory 109 includes a memory store in which physiological signals sensed by the control circuitry 108 can be transiently staged, pending telemetered data download.

The telemetry circuitry 110 provides an interface between the IMD 103 and an external device, such as a programmer, patient management device, or similar device capable of IMD interrogation. For near field data exchange, the IMD 103 communicates through inductive telemetry signals exchanged through a wand placed over the location of the IMD 103. Programming or interrogating instructions are sent to the IMD 103 and the recorded physiological signals are downloaded. For far field data exchange, the IMD 103 communicates through far field telemetry, such as radio frequency (RF) or optical telemetry, as further described below with reference to FIG. 2. Other data interfaces are possible.

Other configurations and arrangements of leads and electrodes can also be used. Furthermore, although described with reference to IMDs for providing cardiac monitoring and therapy delivery, suitable IMDs include other types of implantable therapeutic and monitoring devices in addition to or in lieu of cardiac monitoring and therapy delivery IMDs, including IMDs for providing neural stimulation, drug delivery, and physiometry monitoring and collection.

System

Figure 2:
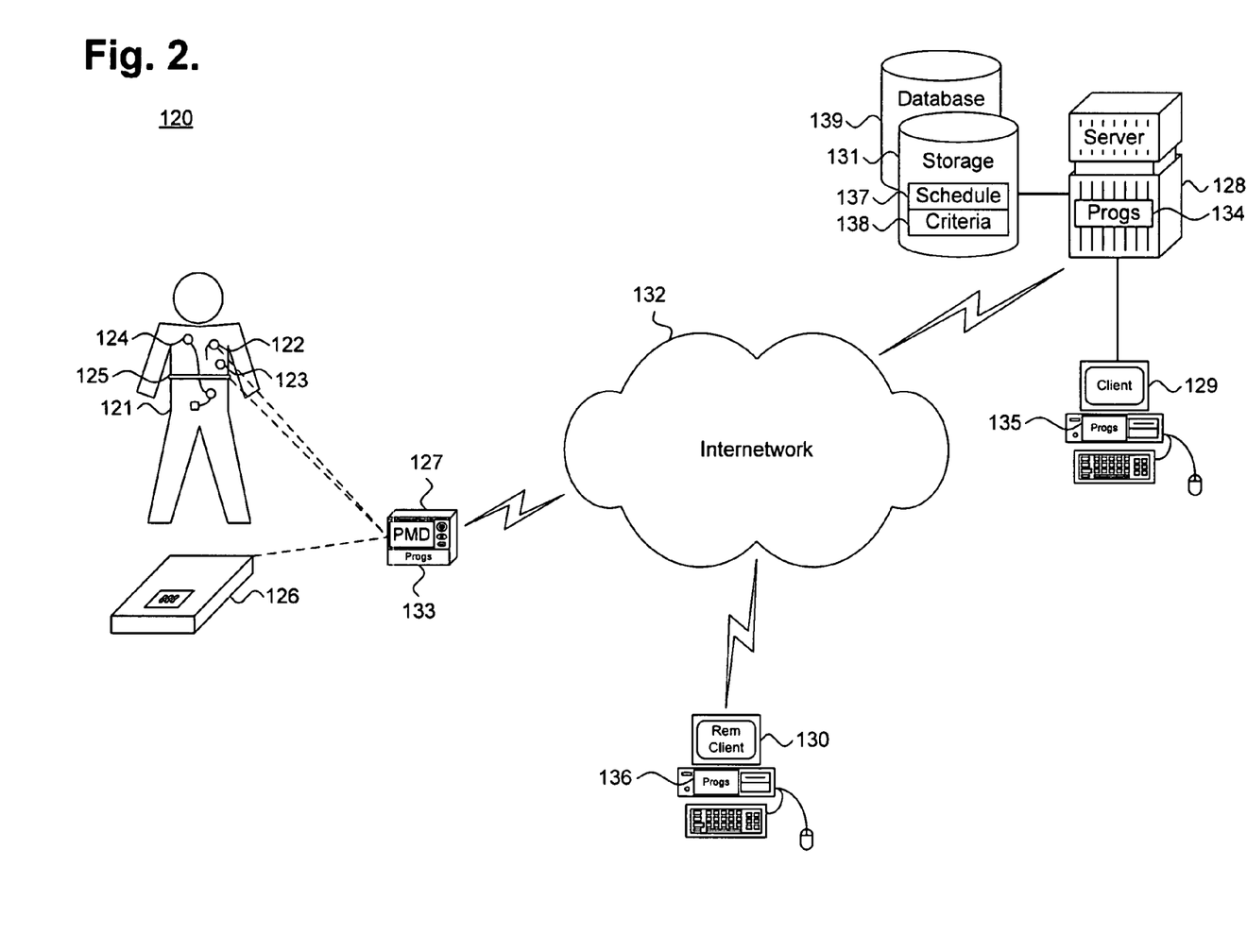
FIG. 2 is a block diagram showing, by way of example, a system for managing locally-initiated medical device interrogation, in accordance with one embodiment.

Automated patient management encompasses a range of activities, including remote patient management and automatic diagnosis of patient health, such as described in commonly-assigned U.S. Patent application Pub. No. US 2004/0103001, pending, published May 27, 2004, the disclosure of which is incorporated by reference. Such activities can be performed proximal to a patient, such as in the patient's home or office; through a centralized server, such as in a hospital, clinic or physician's office; or through a remote workstation, such as a secure wireless mobile computing device. FIG. 2 is a block diagram showing, by way of example, a system for managing locally-initiated medical device interrogation 120, in accordance with one embodiment. An individual patient 121 is remotely managed through a patient management device (PMD) 127, for example, such as described in commonly-assigned U.S. patent application, entitled, "System and Method for Managing Alert Notifications in an Automated Patient Management System," Ser. No. 11/121,870, filed May 3, 2005, pending, the disclosure of which is incorporated by reference. Each patient management device 127 is interconnected remotely over an internetwork 132, such as the Internet, to a centralized server 128, which provides remote patient care. The internetwork 132 can offer both conventional wired and wireless interconnectivity. In one embodiment, the internetwork 132 is based on the Transmission Control Protocol/Internet Protocol (TCP/IP) network communication protocols, although other types or combinations of networking implementations are possible. Similarly, other network topologies and arrangements are possible.

Figure 8:
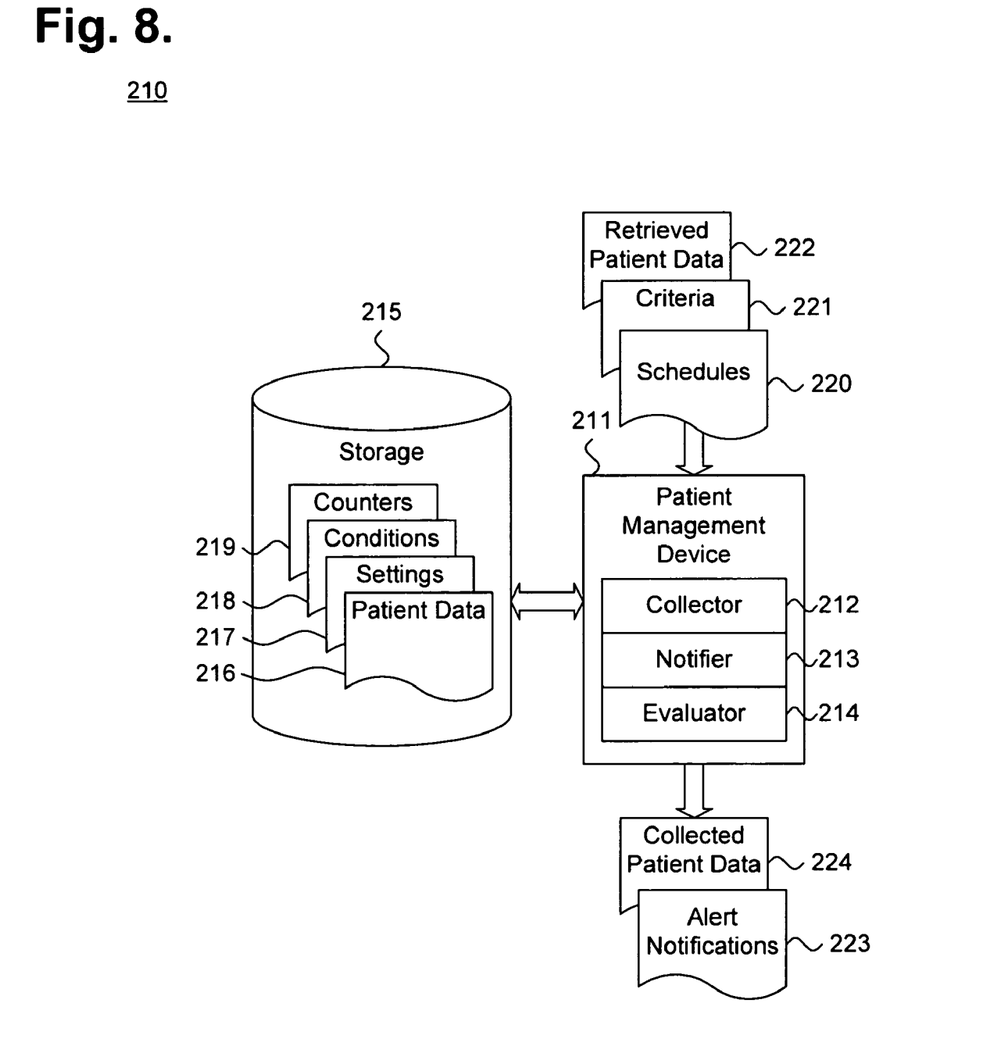
FIG. 8 is a functional block diagram showing a patient management device for use in the system of FIG. 2.

Each patient management device 127 is assigned to an individual patient 121 to provide a localized and network-accessible interface, as further described below with reference to FIG. 8. The patient management device 127 noncontinuously interfaces locally to one or more medical devices 122-126, either through direct means, such as wired serial connectivity, or through indirect means, such as inductive coupled telemetry, optical telemetry, or selective radio frequency or wireless telemetry based on, for example, "strong" Bluetooth or IEEE 802.11 wireless fidelity "WiFi" and "WiMax" interfacing standards. Other configurations and combinations of medical device interfacing are possible. When interfaced, the patient management device 127 is used by the patient to interrogate the medical devices 122-126 to retrieve patient data that has been recorded and transiently staged and, in a further embodiment, to program onboard operational parameters. Other types of patient management device-to-medical device functionality can be provided.

The centralized server 128 serves as both a repository for patient data that has been uploaded from patient management devices 127 and as a patient data evaluator. Patient data includes physiological measures, which can be quantitative or qualitative; parametric data regarding the status and operational characteristics of the medical device itself; and environmental factors and parameters, such as the temperature or time of day. Other types of patient data are possible.

Generally, the medical devices 122-126 collect and forward the patient data either as a primary or supplemental function. Medical devices include, by way of example, medical devices that deliver or provide therapy to the patient 121, sensors that sense physiological data in relation to the patient 121, and measurement devices that measure environmental factors and parameters occurring independent of the patient 121. Specific medical devices include IMDs 122, such as pacemakers, implantable cardiac defibrillators (ICDs), drug pumps, and neuro-stimulators; and EMDs 124, such as automatic external defibrillators (AEDs). Sensors include implantable sensors 123, such as implantable heart and respiratory monitors and implantable diagnostic multi-sensor non-therapeutic devices; and external sensors 125, 126, such as Holter monitors, weight scales, and blood pressure cuffs. Other types of medical, sensing, and measuring devices, both implantable and external, are possible. Each medical device can generate one or more types of patient data and can incorporate one or more components for delivering therapy, sensing patient physiometry, and measuring environmental factors and parameters.

In a further embodiment, data values can be entered by a patient 121 directly into a medical device 122-126 that incorporates a user interface or a patient management device 127. For example, answers to health questions could be input into a measurement device that includes interactive user interfacing means, such as a keyboard and display or a microphone and speaker.

The patient management device 127 retrieves and temporarily stores patient data from the medical devices 122-126 for periodic upload over the internetwork 132 to the centralized server 128 and storage in a database 139. The patient data is retrieved from each medical device 122-126 on a regular basis, such as specified remotely by a caregiver, and locally at the initiative of the patient 121, as further described below respectively with reference to FIGS. 3 and 4. The frequency of scheduled and patient-initiated patient data retrieval can be defined by settings and conditions internally maintained by the patient collection device 127, or in accordance with a schedule 137 and criteria 138 remotely-specified and downloaded to the patient collection device 127. The centralized server 128 maintains the schedule 137 and criteria 138 in a storage device 131.

The collected patient data can be evaluated by either the patient collection device 127 or the centralized server 128 for the occurrence of one or more chronic or acute health conditions, such as described in related, commonly-owned U.S. Pat. No. 6,336,903, to Bardy, issued Jan. 8, 2002; U.S. Pat. No. 6,368,284, to Bardy, issued Apr. 9, 2002; U.S. Pat. No. 6,398,728, to Bardy, issued Jun. 2, 2002; U.S. Pat. No. 6,411, 840, to Bardy, issued Jun. 25, 2002; and U.S. Pat. No. 6,440, 066, to Bardy, issued Aug. 27, 2002, the disclosures of which are incorporated by reference.

In a further embodiment, the frequency of scheduled and patient-initiated patient data retrieval can be remotely defined by one or more locally-configured clients 129 or one or more remote clients 130 securely-interconnected over the internetwork 132. In addition, the clients 129 and remote clients 130 can be used to access and analyze the collected patient data. The clients 129 and remote clients 130 can be used, for example, by caregivers, such as physicians, nurses, or qualified medical specialists, to securely access stored patient data assembled in the database and to select and prioritize patients for health care provisioning, such as respectively described in commonly-assigned U.S. patent application, entitled, "System and Method for Managing Coordination of Assembled Patient Data in an Automated Patient Management System," Ser. No. 11/121,593, filed May 3, 2005, pending, and U.S. patent application, entitled, "System and Method for Managing Patient Triage in an Automated Patient Management System," Ser. No. 11/121,594, filed May 3, 2005, pending, the disclosures of which are incorporated by reference. Although described herein with reference to caregivers, the entire discussion applies equally to organizations, including hospitals, clinics, and laboratories, and other individuals or interests, such as researchers, scientists, universities, and governmental agencies, seeking access to the patient data.

In a further embodiment, patient data is safeguarded against unauthorized disclosure to third parties, including during collection, assembly, evaluation, transmission, and storage, to protect patient privacy and comply with recently enacted medical information privacy laws, such as the Health Insurance Portability and Accountability Act (HIPAA) and the European Privacy Directive. At a minimum, patient health information that identifies a particular individual with health- and medical-related information is treated as protectable, although other types of sensitive information in addition to or in lieu of specific patient health information could also be protectable.

Preferably, the centralized server 128 is a server-grade computing platform configured as a uni-, multi- or distributed processing system, and the clients 129 and remote clients 130 are general-purpose computing workstations, such as a personal desktop or notebook computer. In addition, the patient management device 127, centralized server 128, clients 129, and remote clients 130 are programmable computing devices that respectively execute set of software programs 133, 134, 135, 136 and include components conventionally found in computing device, such as, for example, a central processing unit (CPU), memory, network interface, persistent storage, and various components for interconnecting these components.

Process Flows

Patient data can be collected from the medical devices 122-126 based on a default or caregiver-specified schedule and on locally- or patient-initiated interrogation. The two forms of patient data retrieval are mutually exclusive and changes to the operation of either form of medical device interrogation will not affect the other form of medical device interrogation. In addition, interrogation may require physical action by the patient 121. For instance, where a medical device is interfaced through near field telemetry, such as inductive coupled telemetry, the patient 121 must physically place a wand over the location of the medical device, if implanted. Alternatively, where the medical device is interfaced through far field telemetry, such as optical telemetry or selective radio frequency or wireless telemetry, the patient 121 must ensure that the medical device is within interfacing range of the patient management device 127.

Figure 3:
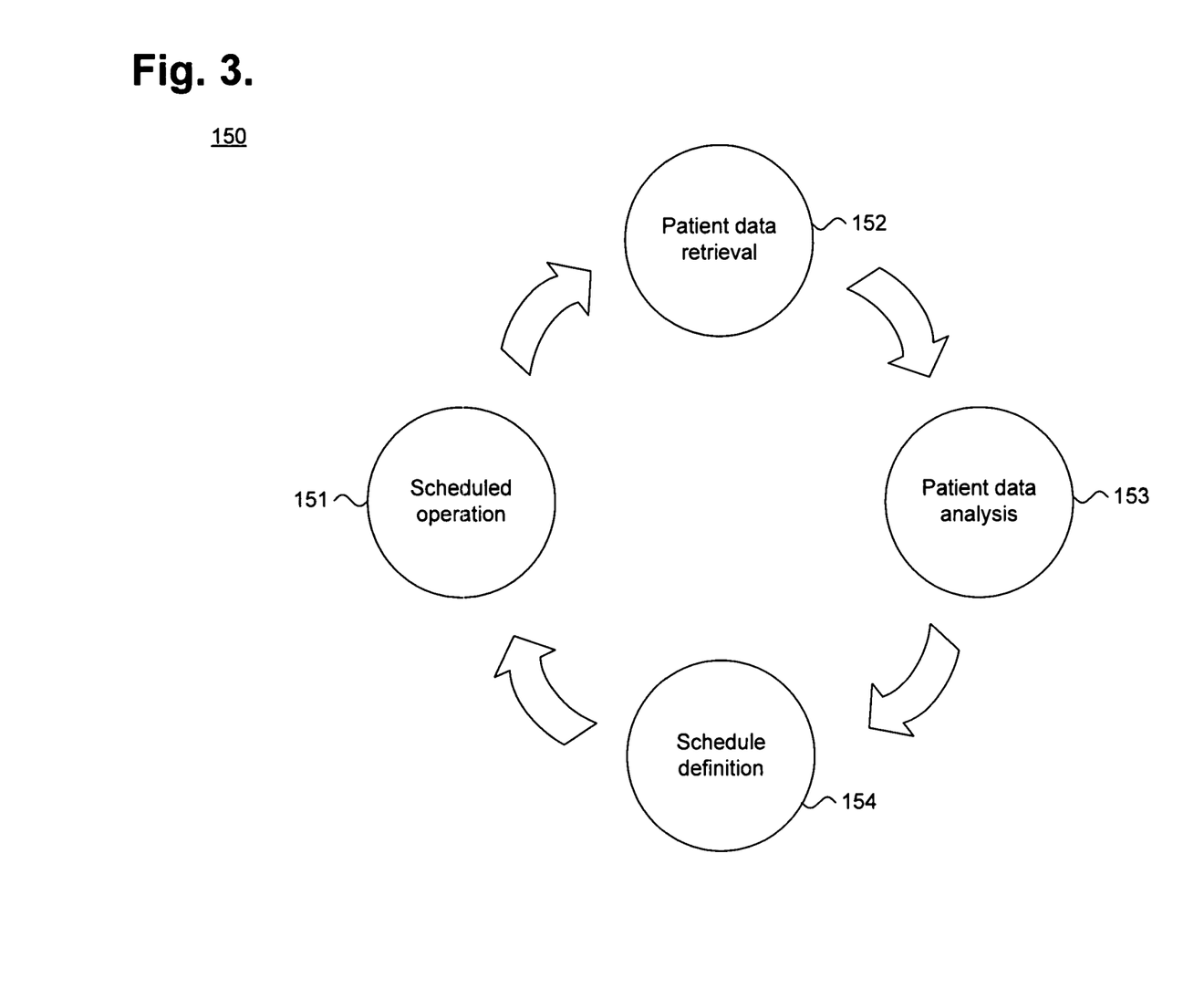
FIG. 3 is a process flow diagram showing scheduled medical device interrogation operation in the system of FIG. 2.

Patient therapy compliance and medical event monitoring is performed through scheduled autonomous patient data retrieval that is performed on a periodic basis. FIG. 3 is a process flow diagram showing scheduled medical device interrogation operation 150 in the system 120 of FIG. 2. Scheduled medical device interrogation occurs at a pre-defined frequency that is defined either by default or by a caregiver (operation 154). In one embodiment, each patient management device 127 includes a factory-configured default medical device interrogation schedule that can be modified at any time, either remotely or locally, based on instructions from a caregiver (operation 154). When necessary, a modified schedule is provided to the patient management device 127 following the most recently-performed patient data upload, thereby effecting near real-time control over scheduled interrogation. The patient management device 127 immediately undertakes modified operation under the modified schedule (operation 151). At each pre-defined interval, the patient management device 127 retrieves patient data from a specified patient medical device 122-126 (operation 152), which is then uploaded to the centralized server 128 or other patient data repository, for storage and analysis (operation 153).

Figure 4:
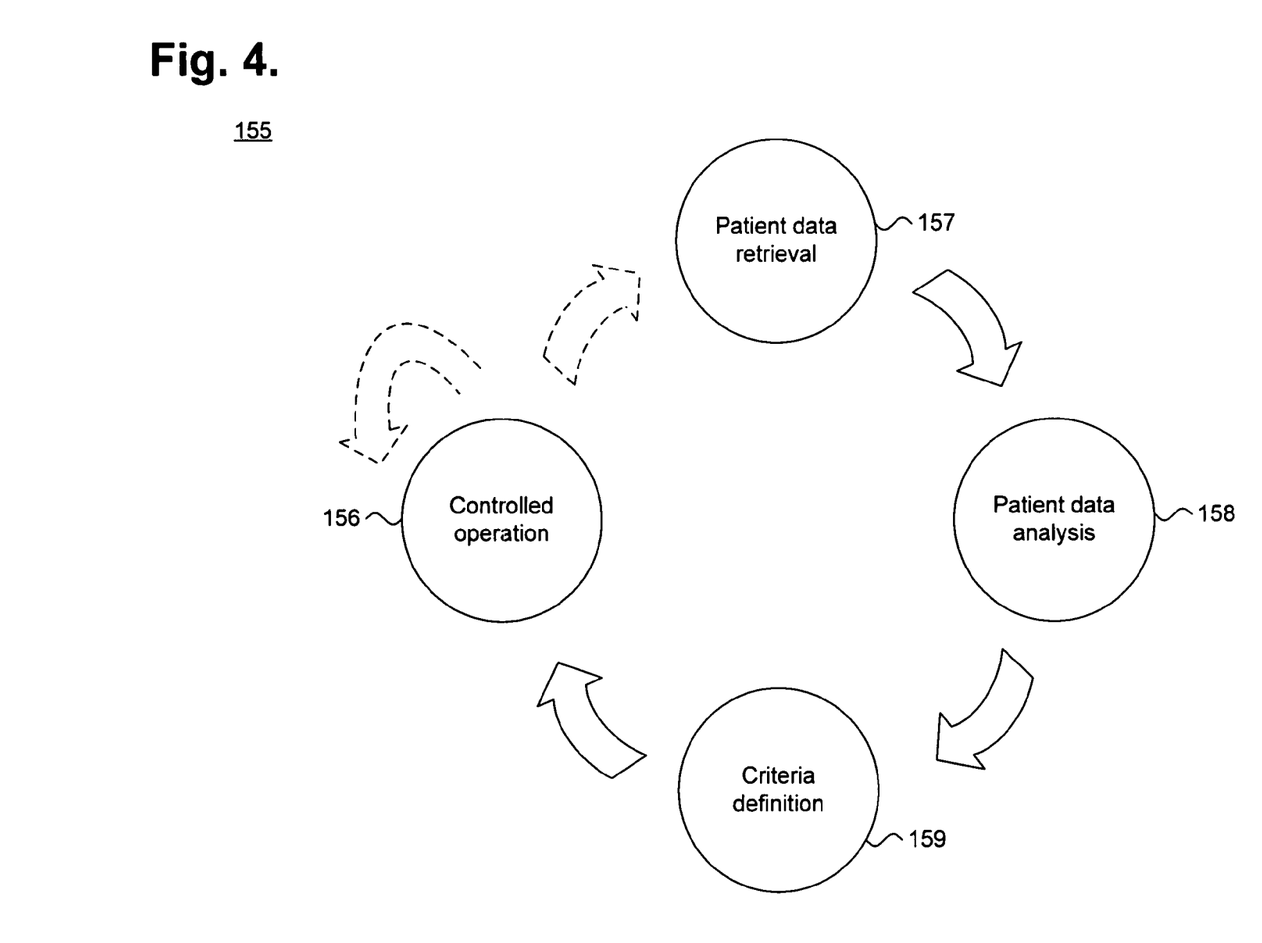
FIG. 4 is a process flow diagram showing controlled medical device interrogation operation in the system of FIG. 2.

Patient-initiated medical device interrogation is triggered locally and occurs at the discretion of the patient, or other individual physically proximal to both the patient 121 and the patient management device 127. FIG. 4 is a process flow diagram showing controlled medical device interrogation operation 155 in the system 120 of FIG. 2. Whether, if, and how many times a patient is allowed to initiate self-interrogation or is blocked from performing self-interrogation is defined through criteria specified by a caregiver (operation 159). The patient management device 127 calls the centralized server 128 prior to allowing or blocking self-interrogation to determine whether a new set of criteria is available. In one embodiment, three criteria for patient-initiated interrogation are provided, although other criteria are possible. First, patient-initiated interrogations can be completely and unconditionally disabled. Second, patient-initiated interrogations can be disabled subject to conditions, which allow the interrogation to proceed, such as a bona fide medical emergency or within a fixed time period following an event occurrence. Third, patient-initiated interrogations can be limited to a fixed number of attempts, after which no further interrogations are allowed, or to a fixed number of attempts within a specified period of time, such as five interrogations per week. Other types of conditional, finite, and evaluateable limits on patient-initiated interrogations are possible.

The criteria, once defined (operation 159), is provided to the patient management device 127 following the most recently-performed patient data upload, thereby effecting near real-time control over patient-initiated interrogation. The patient management device 127 then undertakes controlled operation, subject to the criteria (operation 156). Where permitted, patient data is retrieved and uploaded to the centralized server 128 or other data repository (operation 157), where the patient data is analyzed (operation 158). The criteria remains in effect until changed by the caregiver, either explicitly through set instructions or implicitly through, for instance, the expiration of a fixed time period. Each modified criteria is provided to the patient management device 127.

Method

Figure 5:
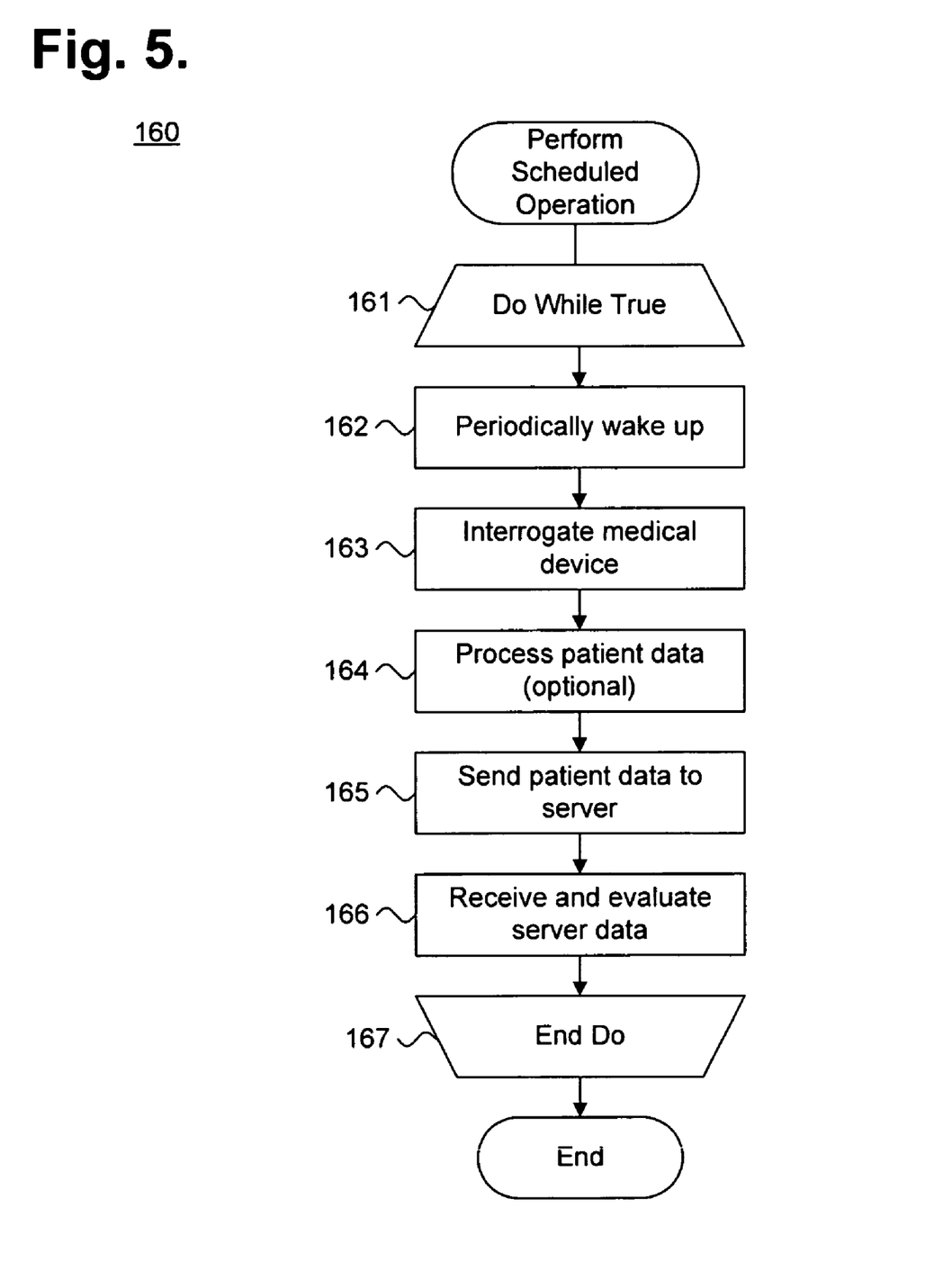
FIG. 5 is a flow diagram showing a method for performing scheduled medical device interrogation, in accordance with one embodiment.

Each medical device 122-126 can be interrogated automatically, per a schedule, or by locally-initiated control, conditioned on a criteria. Autonomous patient data retrieval occurs periodically per a pre-defined schedule 137 that is performed independently from any patient-initiated medical device interrogations. With scheduled autonomous interrogation, the patient management device 127 periodically interrogates associated patient medical devices 122-126 and uploads retrieved patient data. FIG. 5 is a flow diagram showing a method for performing scheduled medical device interrogation 160, in accordance with one embodiment. Each patient management device 127 includes a factory-defined default or caregiver-specified schedule that is received from the centralized server 128 during initial installation.

Scheduled interrogations are performed in a processing cycle (blocks 161-167). During each cycle (block 161), the patient management device 127 periodically "wakes up," that is, enters an active processing state (block 162) and interrogates the medical device to retrieve transiently-staged patient data (block 163). The patient management device 127 can optionally process the patient data (block 164) to identify, for instance, alarm conditions based on threshold or trending analysis. Other forms of patient data processing are possible. The patent data is then sent to the centralized server 128 (block 165) or other patient data repository, for storage and analysis, and any server data, such as modifications to the locally-maintained schedule or criteria, are received and evaluated (block 166). Processing continues with the next cycle (block 167).

Figure 6:
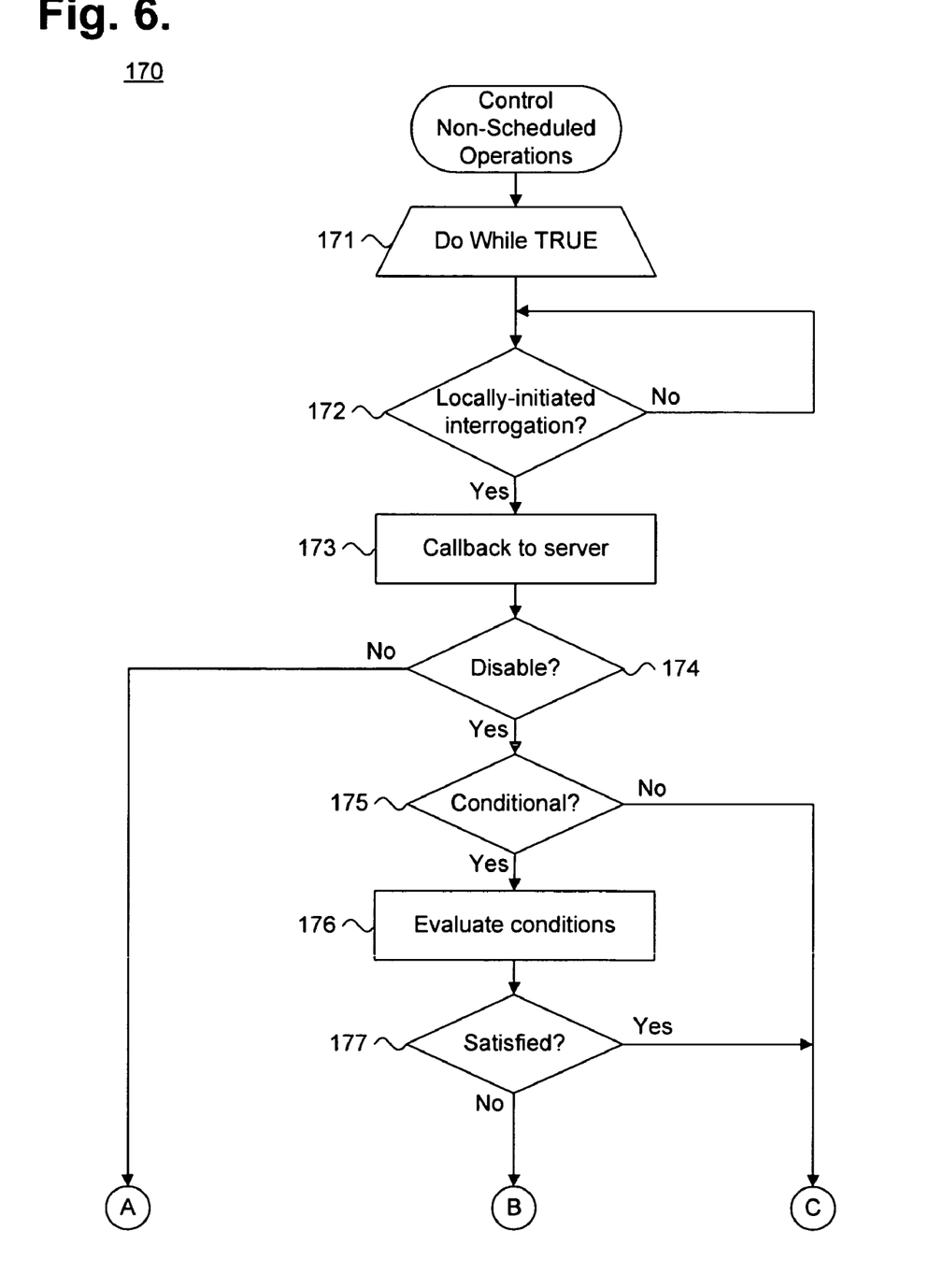
FIG. 6 is a flow diagram showing a method for managing locally-initiated medical device interrogation, in accordance with one embodiment.

Patient-initiated interrogation requires evaluation of pre-defined criteria 138 and server callback before being allowed to proceed. FIG. 6 is a flow diagram showing a method for managing locally-initiated medical device interrogation 170, in accordance with one embodiment. In addition to a schedule, each patient management device 127 also includes a factory-defined default or caregiver-specified criteria that is received from the centralized server 128.

Requests for locally-initiated interrogation are controlled in a processing cycle (blocks 161-167). During each cycle (block 161), a request for a locally-initiated interrogation of a medical device (block 172) results in a callback to the centralized server 128 (block 173) to obtain the most up-to-date criteria for patient-initiated interrogation. If locally-initiated interrogation is disabled in the criteria (operation 174), the patient management device 127 evaluates the three types of control criteria. First, if interrogation is unconditionally disabled (block 175), the medical device interrogation interface is disabled from allowing any patient-initiated interrogation to proceed (block 181), although scheduled autonomous patient data interrogation continues unaffected. Patient-initiated interrogation can be disabled, for instance, by temporarily deactivating an inductive wand or a radio frequency or optical transceiver. Other forms of interrogation disablement are possible. If interrogation is conditionally disabled (block 175), the condition parameters are evaluated to determine whether interrogation can proceed (block 176). For example, the recentness of an event occurrence can be checked. If the conditions for disabling interrogation are satisfied (block 177), the medical device interrogation interface is disabled from allowing any patient-initiated interrogation to proceed (block 181), although scheduled autonomous patient data interrogation continues unaffected. Similarly, if patient-initiated interrogation is not limited to a finite number of interrogation attempts (block 178), the medical device interrogation interface is disabled from allowing any patient-initiated interrogation to proceed (block 181), although scheduled autonomous patient data interrogation continues unaffected. Otherwise, an interrogation counter is evaluated to determine whether interrogation can proceed (block 179). If the limit on the number of interrogation attempts has been exceeded (block 180), the medical device interrogation interface is disabled from allowing any patient-initiated interrogation to proceed (block 181), although scheduled autonomous patient data interrogation continues unaffected. Otherwise, locally-initiated interrogation is allowed and the interrogation interface is enabled (block 182). The patient management device 127 interrogates the medical device to retrieve transiently-staged patient data (block 183). The patient management device 127 can optionally process the patient data (block 184) to identify, for instance, alarm conditions based on threshold or trending analysis. Other forms of patient data processing are possible. The patent data is then sent to the centralized server 128 (block 185) or other patient data repository, for storage and analysis, and any server data, such as modifications to the locally-maintained schedule or criteria, are received and evaluated (block 186). Processing continues with the next cycle (block 187).

Timing

Figure 7:
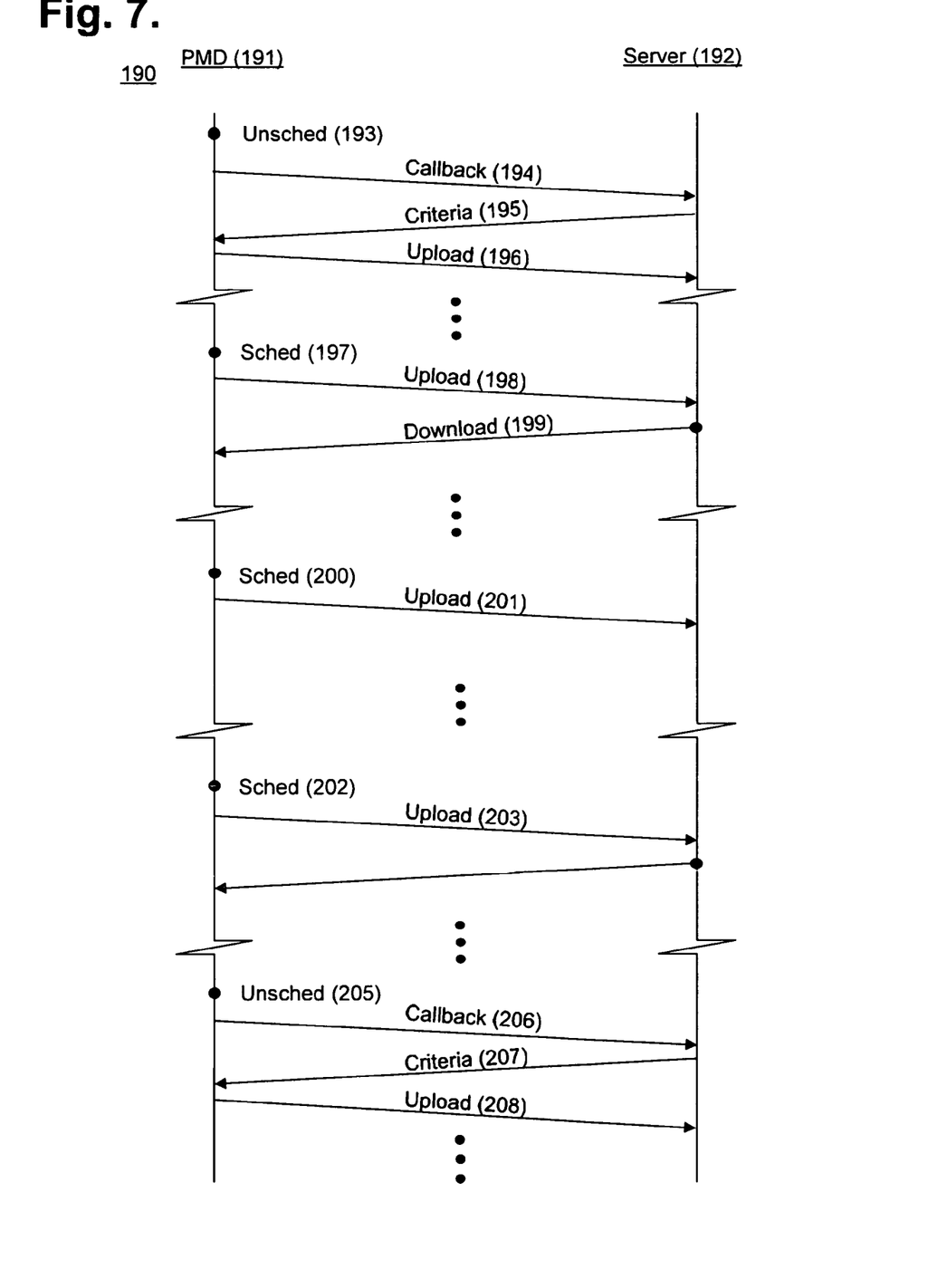
FIG. 7 is a timing diagram showing, by way of example, medical device interrogation management in the system of FIG. 2.

Scheduled autonomous interrogation and patient-initiated interrogation proceed independently, but the processing and execution of both occur together. FIG. 7 is a timing diagram showing, by way of example, medical device interrogation management 190 in the system 120 of FIG. 2. Each unscheduled patient-initiated interrogation 193 on a patient management device 191 results in a server callback 194, which requests download of the most up-to-date criteria 195 for patient-initiated interrogations. If the interrogation is permitted to proceed, retrieved patient data will be sent as an upload 196 to the centralized server 192 or other data repository. Scheduled autonomous interrogations 197, 200, 202 also result in the upload 198, 201, 203 of the retrieved patient data. Modifications to the criteria or schedule, if available, can downloaded 199, 204 from the centralized server 192 to the patient management device 191 whenever the schedule of autonomous patient data retrieval 137 or criteria of patient-initiated patient data retrieval 138 have been modified. Assuming, for instance, that a modified criteria is received in a download 199 following a post-patient data upload 198 and unconditionally disables all further patient-initiated interrogations, scheduled autonomous interrogations 198, 200 and retrieved patient data uploads 199, 201 will continue until, and if, the criteria is again modified and received in a download 202 to the patient management device 191. Assuming that the unconditional interrogation disablement has been lifted, unscheduled patient-initiated patient data retrieval 205 and retrieved patient data upload 208 can then proceed, when requested, including server callback 206 and download of the most up-to-date criteria 207.

Patient Management Device Structure

Each patient management device functions as the central hub for the remote management of individual patients. FIG. 8 is a functional block diagram showing a patient management device 211 for use in the system 120 of FIG. 2. In one embodiment, the patient management device 211 executes a sequence of programmed process steps, such as described above beginning with reference to FIGS. 3 and 4, implemented, for instance, on a programmed digital computer system.

The patient management device 211 includes a storage device 215 and can be configured to collect patient data, provide alert notifications, and, in a further embodiment, evaluate the collected patient data. Other patient management device functions are possible.

The patient management device 211 stores patient data 216, settings 217, conditions 218, and counters 219 in the storage device 215. The patient data 216 contains retrieved patient data 222 that is being temporarily stored by the patient management device 211, pending patient data upload to the centralized server 128. The settings 217, conditions 218, and counters 219 control patient data collection and respectively define scheduled frequency and patient-initiated interrogation control, conditions affecting patient-initiated interrogation, and limits on number of permissible patient-initiated interrogations. As the patient management device 211 receives schedules 220 and criteria 221 from the centralized server 128 or, in a further embodiment, via a user interface, the settings 217, conditions 218, and counters 219 are set to effect near real-time changes in patient data collection. The settings for scheduled frequency 217 identify the frequency and types of patient data to be collected as part of routine patient following. Conversely, the settings for patient-initiated interrogation control 217 specify whether such interrogation is unconditionally disabled, disabled subject to one or more conditions 218, or limited to a pre-defined number of interrogations by a set of counters 219. The settings for scheduled frequency 217 operate independently of all other settings, conditions, and counters.

The patient management device 211 includes a collector 212, notifier 213, and evaluator 214. When operating under a schedule 220, the collector 212 autonomously interrogates and retrieves patient data from the medical devices 122-126. In one such embodiment, the collector has a schedule-driven interrogator to periodically retrieve the patient data by interfacing to and interrogating the medical device per a pre-defined schedule defining autonomous patient data retrieval frequency. When operating under a criteria 221, the collector 212 only permits the patient to interrogate and retrieve patient data from the medical devices 122-126 if the pertinent settings 217, conditions 218, and counters 219 allow. However, the patient management device 127 first calls the centralized server 128 prior to allowing or blocking self-interrogation to determine whether a new or modified set of criteria 221 is available. In one such embodiment, the collector has a criteria-driven interrogator to permit further retrieval of the patient data independent of the pre-defined schedule by enabling operation of the interface based on a remotely-specifiable criteria for controlling patient-initiated patient data retrieval.

In a further embodiment, the collector 212 can execute a follow-up scheme, for example, by sending follow-up requests to the medical devices 122-126, if possible, that have not sent expected patient data, or by sending a message or other communication to the patient 121, caregiver, or authorized third party as a compliance notification. Finally, the collector 212 uploads the collected patient data 224 to the centralized server 128, either immediately upon retrieval or after a maximum delay to allow the patient data 216 to accumulate.

Depending upon the context, the notifier 213 provides alert notifications 223 to the patient 121, caregiver, or authorized third party. Alert notifications 223 can be assigned, for instance, to notification schemes, which are executed upon the detection of an associated condition or alert trigger. For example, upon each interrogation attempt, the patient 121 could be informed that the caregiver has temporarily disabled patient-initiated interrogations and to call emergency medical services when the patient-initiated interrogation function has been disabled or the allotted number of interrogations has been exceeded. In a further embodiment, the notification schemes can be organized into one or more levels of alerts. For instance, each week, the caregiver could be notified of the number of unscheduled interrogations attempted and the number of times that a limit on interrogations has been exceeded.

Finally, in a further embodiment, the evaluator 214 evaluates the retrieved patient data 222 against a subset of alert conditions, which can include one or more triggers that are associated with the alert conditions. Occurrences of the alert condition will set off the associated triggers or could trigger further patient data collection. The same alert conditions can be evaluated by both the patient management device 211 and the centralized server 128. Other forms of patient management device functionality are possible.

While the invention has been particularly shown and described as referenced to the embodiments thereof, those skilled in the art will understand that the foregoing and other changes in form and detail may be made therein without departing from the spirit and scope of the invention.

What is claimed is:

1. A system for managing locally-initiated medical device interrogation, comprising:
   a noncontinuously coupleable interface over which to retrieve patient data recorded and transiently staged by a medical device monitoring physiological measures of a patient; and
   a collector, configured to:
   periodically retrieve the patient data by interfacing to and interrogating the medical device per a pre-defined schedule defining autonomous patient data retrieval frequency; and
   permit patient-initiated patient data retrieval independent of the pre-defined schedule;
   wherein the system is configured to:
   store remotely-specifiable criteria specified by a caregiver;
   control patient-initiated patient data retrieval in accordance with the criteria; and
   receive modifications to the remotely-specifiable criteria in response to an attempted further retrieval of the patient data.

2. A system according to claim 1, further comprising one of:
   a disablement control to disable the interface operation by limiting a number of times that the interface operation is enabled indefinitely or over a fixed period of time.

3. A system according to claim 2, wherein a manual override of the interface operation disabling is allowed.

4. A system according to claim 1, further comprising:
   a notifier to track attempts at patient-initiated patient data retrieval excluded by the remotely-specifiable criteria.

5. A system according to claim 1, wherein the pre-defined schedule is provided from at least one of an external source and a default local parameter set.

6. A system according to claim 1, wherein the remotely-specifiable criteria is modified on at least one of: a one-time basis and periodically.

7. A system according to claim 1, further comprising:
   a storage manager to provide the retrieved patient data to an external repository on a regular basis.

8. A system according to claim 7, wherein modifications to the remotely-specifiable criteria are received contemporaneous to the retrieved patient data.

9. A system according to claim 1, further comprising:
   a notifier to display a message to the patient in response to an attempt at patient-initiated patient data retrieval that has been excluded by the remotely-specifiable criteria.

10. A system according to claim 1, wherein the medical device comprises an implantable medical device.

11. A system according to claim 1, wherein the patient data is retrieved from the medical device through interfacing selected from the group consisting of: inductive telemetry, radio frequency telemetry, optical telemetry, and physical connectivity.

12. A method for managing locally-initiated medical device interrogation, comprising:
    providing a noncontinuously coupleable interface over which to retrieve patient data recorded and transiently staged by a medical device monitoring physiological measures of a patient;
    periodically retrieving the patient data by interfacing to and interrogating the medical device per a pre-defined schedule defining autonomous patient data retrieval frequency;
    controlling patient-initiated patient data retrieval independent of the pre-defined schedule based on a remotely-specifiable criteria specified by a caregiver; and
    receiving modifications to the remotely-specifiable criteria in response to an attempted further retrieval of the patient data.

13. A method according to claim 12, further comprising one of:
    disabling the interface operation; and
    limiting a number of times that the interface operation is enabled indefinitely or over a fixed period of time.

14. A method according to claim 13, further comprising:
    allowing a manual override of the interface operation disabling.

15. A method according to claim 12, further comprising:
    tracking attempts at patient-initiated patient data retrieval excluded by the remotely-specifiable criteria.

16. A method according to claim 12, further comprising:
    providing the pre-defined schedule from at least one of an external source and a default local parameter set.

17. A method according to claim 12, further comprising:
    modifying the remotely-specifiable criteria on at least one of: a one-time basis and periodically.

18. A method according to claim 12, further comprising:
    providing the retrieved patient data to an external repository on a regular basis.

19. A method according to claim 18, further comprising:
    receiving modifications to the remotely-specifiable criteria contemporaneous to the retrieved patient data.

20. A method according to claim 12, further comprising:
    displaying a message to the patient in response to an attempt at patient-initiated patient data retrieval that has been excluded by the remotely-specifiable criteria.

21. The method according to claim 12 wherein the medical device comprises an implantable medical device.

22. A method according to claim 12, further comprising:
    retrieving the patient data from the medical device through interfacing selected from the group consisting of: inductive telemetry, radio frequency telemetry, optical telemetry, and physical connectivity.

23. A computer-readable storage medium holding code for performing the method according to claim 12.

24. An apparatus for managing locally-initiated medical device interrogation, comprising:
    means for providing a noncontinuously coupleable interface over which to retrieve patient data recorded and transiently staged by a medical device monitoring physiological measures of a patient;
    means for periodically retrieving the patient data by means for interfacing to and means for interrogating the medical device per a pre-defined schedule defining autonomous patient data retrieval frequency; and
    means for controlling locally patient-initiated patient data retrieval independent of the pre-defined schedule based on a remotely-specifiable criteria specified by a caregiver; and
    means to receive modifications to the remotely-specifiable criteria in response to an attempted further retrieval of the patient data.

* * * * *